United States Patent
Hirata et al.

(10) Patent No.: US 7,355,064 B2
(45) Date of Patent: Apr. 8, 2008

(54) METHOD FOR PREPARING 15-KETO-PROSTAGLANDIN E DERIVATIVE

(75) Inventors: Ryu Hirata, Chiyoda-ku (JP); Tatsuya Matsukawa, Chiyoda-ku (JP)

(73) Assignee: R-Tech Ueno, Ltd., Tokyo-to (JP)

( * ) Notice: Subject to any disclaimer, the term of this patent is extended or adjusted under 35 U.S.C. 154(b) by 0 days.

(21) Appl. No.: 11/703,098

(22) Filed: Feb. 7, 2007

(65) Prior Publication Data
US 2007/0185206 A1 Aug. 9, 2007

Related U.S. Application Data

(60) Provisional application No. 60/765,748, filed on Feb. 7, 2006.

(51) Int. Cl.
*C07C 69/74* (2006.01)
*C07C 61/06* (2006.01)

(52) U.S. Cl. ............................ 560/122; 562/504

(58) Field of Classification Search ............... None
See application file for complete search history.

(56) References Cited

U.S. PATENT DOCUMENTS

| | | | |
|---|---|---|---|
| 4,033,989 A | * | 7/1977 | Bundy ............... 554/214 |
| 4,473,587 A | | 9/1984 | Muryobayashi et al. |
| 5,166,174 A | | 11/1992 | Ueno et al. |
| 5,225,439 A | | 7/1993 | Ueno et al. |
| 5,256,696 A | * | 10/1993 | Ueno et al. ............ 514/573 |
| 5,284,858 A | | 2/1994 | Ueno et al. |
| 5,380,709 A | | 1/1995 | Ueno et al. |
| 5,428,062 A | | 6/1995 | Ueno et al. |
| 5,739,161 A | | 4/1998 | Ueno |
| 5,886,034 A | | 3/1999 | Ueno et al. |

\* cited by examiner

*Primary Examiner*—Paul A. Zucker
(74) *Attorney, Agent, or Firm*—Sughre Mion, PLLC (57) ABSTRACT

Disclosed is an improved method for preparing 15-keto-prostaglandin E derivative. According to the invention, the deprotection of protected hydroxy group required in manufacturing a 15-keto-prostaglandin derivative is conducted under the presence of a phosphoric acid compound.

7 Claims, 2 Drawing Sheets

METHOD FOR PREPARING 15-KETO-PROSTAGLANDIN E DERIVATIVE

CROSS REFERENCE TO RELATED APPLICATION

This application claims the benefit of U.S. Provisional Application No. 60/765,748 filed Feb. 7, 2006.

FIELD OF THE INVENTION

The present invention relates to a method for preparing 15-keto-prostaglandin E derivatives that are useful for the treatment of a variety of diseases or conditions, or as synthesis intermediates for manufacturing therapeutically active compounds.

ART RELATED

Prostaglandin has a prostanoic acid structure indicated by the formula:

(A)

and there are many prostaglandins having a variety of therapeutic effects.

Some synthetic analogues have modified skeletons. PGs are classified into several types according to the structure and substituents on the five-membered ring. For example, Prostaglandins of the A series (PGAs):

Prostaglandins of the B series (PGBs):

Prostaglandins of the C series (PGCs):

Prostaglandins of the D series (PGDs):

Prostaglandins of the E series (PGEs):

, and

Prostaglandins of the F series (PGFs):

are known.

Further, they are classified into $PG_1s$ having a 13,14-double bond; $PG_2s$ having 5,6- and 13,14-double bonds; and $PG_3s$ having 5,6-, 13,14- and 17,18-double bonds.

Prostaglandin Es(PGEs) are prostaglandins having an oxo group at position 9 and a hydroxy group at position 11. PGEs are easily decomposed to give PGAs because the β-elimination of hydroxy group at position 11 of the PGEs is promoted by the presence of carbonyl group at position 9.

In manufacturing prostaglandin derivatives, protection and deprotection of the hydroxy group are necessary. Deprotection of the protected hydroxy group at position 11 by acidic hydrolysis has been well known (see U.S. Pat. No. 4,473,587, the cited reference is herein incorporated by reference). The acidic hydrolysis step may be carried out, for example, (1) with an aqueous solution of an organic acid such as acetic acid, propionic acid, oxalic acid or p-toluenesulfonic acid, or an aqueous solution of an inorganic acid, such as hydrochloric acid or sulfuric acid, advantageously in the presence of a water-miscible organic solvent such as a lower alkanol such as methanol or ethanol, or an ether such as 1,2-dimethoxyethane, dioxane or tetrahydrofuran, at a temperature ranging from ambient to 75° C., or (2) with an anhydrous solution of an organic acid such as p-toluenesulfonic acid or trifluoroacetic acid in a lower alkanol such as methanol or ethanol at a temperature ranging from 10° C. to 45° C. Formerly, deprotection of protected hydroxy group of PGEs was conducted by dissolving the compound to be deprotected in a mixture of acetic acid-tetrahydrofurane-water and heating at about 45 to 50° C. (U.S. Pat. No. 5,739,161, the content of the reference is herein incorporated by reference).

SUMMARY OF THE INVENTION

An object of the instant application is to provide an improved method for hydrolyzing or deprotecting intermediate of a 15-keto-prostaglandin E derivative having a protected hydroxy group to give the desired 15-keto-prostaglandin E derivative, which can be conducted under mild condition and causes less or almost no production of byproduct, prostaglandin A derivative.

Accordingly, the present invention provides a method for manufacturing a 15-keto-prostaglandin E derivative represented by formula (I):

(I)

wherein,

$R_1$ is a saturated or unsaturated bivalent lower or medium aliphatic hydrocarbon residue, which unsubstituted or substituted with halogen, lower alkyl, hydroxy, oxo, aryl or heterocyclic, and at least one of carbon atom in the aliphatic hydrocarbon is optionally substituted by oxygen, nitrogen or sulfur;

$R_2$ is a saturated or unsaturated lower or medium aliphatic hydrocarbon, which is unsubstituted or substituted with lower alkyl, lower alkoxy, lower alkanoyloxy, cyclo(lower)alkyl, cyclo(lower)alkyloxy, aryl, aryloxy, heterocyclic or heterocyclicoxy group; cyclo(lower)alkyl; cyclo(lower)alkyloxy; aryl; aryloxy; heterocyclic; or heterocyclicoxy group;

B is —$CH_2$—$CH_2$—, —CH=CH— or —C≡C—;

Q is —$CH_3$, —$COCH_3$, —OH, —COOH or a functional derivative thereof;

$X_1$ and $X_2$ are hydrogen, lower alkyl, or halogen which comprises the step of hydrolyzing the compound represented by formula (II):

(II)

wherein, $A_1$ is a protecting group for hydroxy group, $R_1$, $R_2$, B, Q, $X_1$ and $X_2$ are the same as above in the presence of phosphoric acid compound.

PREFERRED EMBODIMENT OF THE INVENTION

In the above formula, the term "unsaturated" in the definitions for $R_1$ and $R_2$ is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 6 to 10 carbon atoms for $R_1$ and 1 to 10, especially 1 to 8 carbon atoms for $R_2$.

The term "halogen" covers fluorine, chlorine, bromine and iodine.

The term "lower" is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, sec-butyl, t-butyl, pentyl and hexyl.

The term "lower alkoxy" refers to a group of lower alkyl-O—, wherein lower alkyl is as defined above.

The term "lower alkanoyloxy" refers to a group of RCO—O—, wherein RCO— is an acyl, such as acetyl, generated by oxidation of the above defined lower alkyl The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen and halo(lower)alkyl, wherein halogen atom and lower alkyl are as defined above.

The term "aryloxy" refers to a group represented by the formula ArO—, wherein Ar is aryl as defined above.

The term "heterocyclic" may include mono- to tri-cyclic, preferably monocyclic heterocyclic group which is 5 to 14, preferably 5 to 10 membered ring having optionally substituted carbon atom and 1 to 4, preferably 1 to 3 of 1 or 2 types of hetero atoms selected from nitrogen, oxygen and sulfur. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl and phenothiazinyl. Examples of the substituent include halogen, and halogen substituted lower alkyl, wherein halogen and lower alkyl are as described above.

The term "heterocyclicoxy" means a group represented by the formula HcO—, wherein Hc is a heterocyclic group as described above.

The term "functional derivative" of Q includes salts, preferably pharmaceutically acceptable salts, ethers, esters and amides.

Suitable "pharmaceutically acceptable salts" include salts formed with non-toxic bases conventionally used in pharmaceutical field, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethylmonoethanolamine salt, procaine salt and caffeine salt), a basic amino acid salt (such as arginine salt and lysine salt), tetraalkyl ammonium salt and the like. These salts may be prepared by a conventional process, for example by reacting corresponding acid and base or by conducting salt interchange.

Examples of the ethers include alkyl ethers, for example, lower alkyl ethers such as methyl ether, ethyl ether, propyl ether, isopropyl ether, butyl ether, isobutyl ether, sec-butyl, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-dimethoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, sec-butyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxyethyl ester and 1-methoxyethyl ester; and optionally substituted aryl esters such as, for example, phenyl ester, tolyl ester, t-butylphenyl ester, salicyl ester, 3,4-dimethoxyphenyl ester and benzamidophenyl ester; and aryl(lower)alkyl ester such as benzyl ester, trityl ester and benzhydryl ester.

The amide of Q means a group represented by the formula —CONR'R", wherein each of R' and R" is hydrogen, lower alkyl, aryl, alkyl- or aryl-sulfonyl, lower alkenyl or lower alkynyl, and may be, for example, lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred example of Q is —COOH, its pharmaceutically acceptable salt, ester or amide thereof.

Preferred B is —$CH_2$—$CH_2$— which provides a derivative so called 13,14-dihydro-type PGE.

Preferred $R_1$, is hydrocarbon residue containing 1 to 10 carbon atoms, preferably 6 to 10 carbon atoms. Further, at least one carbon atom in the aliphatic hydrocarbon is optionally replaced by oxygen, nitrogen or sulfur.

Examples of $R_1$ include, for example, the following groups:

Preferred $R_2$ is hydrocarbon containing 1 to 10 carbon atoms, more preferably, 1-8 carbon atoms.

At least one of X1 and $X_2$ is halogen, preferably both are halogen, and especially, both of $X_1$ and $X_2$ are fluorine, which provide a derivative so called 16,16-difluoro type PGE.

$A_1$ is a functional group introduced into the molecule to inactivate and protect the hydroxy group from undesired reactions, and will be replaced with a hydrogen atom by the subsequent acidic hydrolysis. Any of known protecting groups for hydroxy group may be used in the application unless it impairs the object of the invention. Examples of the protecting group or $A_1$ may include tetrahydropyranyl, methoxymethyl, t-butoxymethyl, 1-ethoxyethyl, 1-methoxy-1-methyl-ethyl, benzyloxymethyl, 2-methoxyethoxymethyl, 2,2,2-trichloroethoxymethyl, t-butyldimethylsilyl, triethylsilyl, triisopropylsilyl and diphenylmethylsilyl.

The 15-keto-PG derivative used in the present invention may be in the keto-acetal equilibrium by formation of a hemiacetal between hydroxy at position 11 and keto at position 15.

For example, it has been revealed that when both of $X_1$ and $X_2$ are halogen, especially, fluorine, a tautomeric isomer of the compound, bicyclic compound, exists.

If such tautomeric isomers as above exist, the proportion of both tautomeric isomers varies with the structure of the rest of the molecule or the kind of the substituent present. Sometimes one isomer may predominantly be present in comparison with the other. However, it is to be appreciated that the 15-keto-PGE derivatives used in the present invention cover both isomers.

The bicyclic compound is represented by formula (III):

it is to be noted that such structure or name does not intend to exclude the acetal type compound. In the present invention, any of isomers such as the individual tautomeric isomers, the mixture thereof, or optical isomers, the mixture thereof, a racemic mixture, and other steric isomers may be used in the same purpose.

It has been known that 13,14-dihydro-15-keto-prostaglandin E having the formula as shown below (Tautomer I) may be in equilibrium with its tautomeric isomer (tautomer II) (See U.S. Pat. Nos. 5,166,174, 5,225,439, 5,284,858, 5,380,709, 5,428,062 and 5,886,034, the contents of these references are herein incorporated by reference.).

Tautomer I                    Tautomer II

It is considered that the halogen atom(s) at $X_1$ and/or $X_2$ promote bi-cyclic ring formation, such as the compound A or B below. In addition, in the absence of water, the tautomeric compounds as above exist predominantly in the form of the bi-cyclic compound. In aqueous media, it is supposed that hydrogen bonding occurs between the water molecule and, for example, the keto group on the hydrocarbon chain, thereby hindering bi-cyclic ring formation. The bi-cyclic/mono-cyclic structures, for example, may be present in a ratio of 6:1 in $D_2O$; 10:1 in $CD_3OD-D_2O$ and 96:4 in $CDCl_3$. In the instant specification and claims, tautomeric mixture containing the bi-cyclic compound in a ratio even greater to substantially 100% bi-cyclic compound is within this invention.

Embodiments of the above described bi-cyclic compounds include the Compounds A and B shown below.

Compound A:

wherein,

Q is —$CH_3$, or —$COCH_3$, —OH, —COOH or a functional derivative thereof;

$X_1$ and $X_2$ are hydrogen, lower alkyl, or halogen;

$R_1$ is a saturated or unsaturated bivalent lower or medium aliphatic hydrocarbon residue, which is unsubstituted or substituted with halogen, lower alkyl, hydroxy, oxo, aryl or heterocyclic, and at least one of carbon atoms in the aliphatic hydrocarbon is optionally substituted by oxygen, nitrogen or sulfur; and

$R_2$ is a saturated or unsaturated lower or medium aliphatic hydrocarbon, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic or heterocyclicoxy; cyclo(lower)alkyl; cyclo(lower)alkyloxy; aryl; aryloxy; heterocyclic; or heterocyclicoxy.

While the compounds used in the invention may be represented by a formula or name based on the keto-type structure regardless the presence or absence of the isomers, 7-[(1R,3R,6R,7R)-3-(1,1-difluoropentyl)-3-hydroxy-2-oxabicyclo[4.3.0]nonane-8-one-7-yl] heptanoic acid <7-[(2R,4aR,5R,7aR)-2-(1,1-difluoropentyl)-2-hydroxy-6-oxooctahydrocyclopenta[b]pyran-5-yl]heptanatoic acid>

Compound B:

7-{(1R,6R,7R)-3-[(3S)-1,1-difluoro-3-methylpentyl]-3-hydroxy-2-oxabicyclo[4.3.0]nonane-8-one-7-yl}heptanoic acid <7-{(4aR,5R,7aR)-2-[(3S)-1,1-difluoro-3-methylpentyl]-2-hydroxy-6-oxooctahydrocyclopenta[b]pyran-5-yl}heptanatoic acid>

According to the present invention, the hydrolytic reaction is conducted under the presence of a phosphoric acid compound. By employing phosphoric acid, the hydrolytic reaction of the invention can be conducted under ambient temperature and the desired de-protected product, 15-keto-prostaglandin E derivative can be obtained within a short period of time causing less or no production of the by-product, prostaglandin A derivative. The phosphoric acid used in the present invention is an oxo acid produced by hydrolytic degradation of $P_4O_{10}$. Examples of phosphoric acid compound may include phosphoric acid and strong phosphoric acid such as orthophosphoric acid, diphosphoric acid (pyrophosphoric acid), triphosphoric acid, tetraphosphoirc acid and a mixture thereof. Among them, phosphoric acid is especially preferable.

The amount of the phosphoric acid compound used in the hydrolytic reaction of the present invention is not limited and the art should determine the optimal amount. For example, when 85% aqueous phosphoric acid solution is used, the amount of the solution may be 0.5 to 1.5 part by volume (in ml) per one part by weight (in g) of the compound of formula (II).

The reaction is preferably conducted in a mixed solvent comprising water and organic solvent. The organic solvent used in the hydrolytic reaction of the invention may be any solvent which can dissolve therein the compound of formula (II) and is miscible with water. Examples organic solvents may include nitrites such as acetonitrile, ethers such as tetrahydrofuran, dioxane and dimethoxyethane, and alcohols such as methanol, ethanol and propanol. Acetonitrile is especially preferable.

The mixing ratio between water and the organic solvent may be in the range wherein the amount of water is 0.5 to 1.5 parts by volume (in ml) per one part by weight (in g) of the compound of formula (II), and the amount of the organic solvent is 1 to 15, preferably, 8 to 12 parts by volume (in ml) per one part by weight (in g) of the compound of formula (II).

The hydrolytic reaction may be conducted at a temperature about 0 to 35° C., preferably, 10 to 30° C. The reaction time may be about 1 to 6 hours, especially, 2 to 4 hours.

The instant invention will be further illustrated by the examples and test examples shown below. The examples are only for illustration and should not be used for limiting the scope of the invention.

EXAMPLE 1

To a solution of benzyl 7-[(1R,2R,3R)-2-(4,4-difluoro-3-oxooctyl)-5-oxo-3-(2-tetrahydropyranyloxy) cyclopentyl] heptanoate (1) (70.49 g, 124.8 mmol) in acetonitrile (705 ml), water (70.5 ml) and 85% aqueous phosphoric acid (70.5 ml) were added, and the mixture was stirred for three hours at about 20° C. 10% aqueous sodium chloride (705 ml) was added to the mixture and the mixture was extracted with ethyl acetate (276 ml) for 3 times. The organic layers were combined and washed with 10% aqueous sodium chloride (360 ml), saturated aqueous sodium bicarbonate (360 ml) and saturated aqueous sodium chloride (360 ml) successively, dried with anhydrous magnesium sulfate (51 g) and concentrated under reduced pressure. The residue was purified by silica gel column chromatography (Fuji Silysia BW-300 2100 g, ethyl acetate:hexane=1:4). Fractions containing impurities were purified again by silica gel column chromatography (Fuji Silysia BW-300 1000 g, ethyl acetate: hexane=1:4) to give benzyl 7-[(2R,4aR,5R,7aR)-2-(1,1-difluoropentyl)-2-hydroxy-6-oxooctahydrocyclopenta[b]pyran-5-yl]heptanate (2) (52.64 g, 109.5 mmol, yield: 87.8%).

COMPARATIVE EXAMPLE 1

Conventional Method Using Acetic Acid.

-continued 75.8%

2

To a solution of benzyl 7-[(1R,2R,3R)-2-(4,4-difluoro-3-oxooctyl)-5-oxo-3-(2-tetrahydropyranyloxy) cyclopentyl] heptanoate (1) (39.84 g, 70.54 mmol) in tetrahydrofuran (40 ml), acetic acid (260 ml) and water (140 ml) were added. The mixture was stirred at about 40° C. for 4 hours. The reaction was concentrated under reduced pressure and the residue was purified by silica gel column chromatography (Fuji Silysia BW-300 1600 g, ethyl acetate:hexane=1:3). Fractions containing impurities were purified again by silica gel column chromatography (Fuji Silysia FL-60D 1600 g, ethyl acetate:hexane=1:4). Fractions still containing impurities were collected and further purified repeatedly with silica gel column chromatography (Fuji Silysia FL-60D 1000 g, IPA:hexane=8:100), (Fuji Silysia FL-60D 1600 g, IPA:hexane=7.5:100→3:40), (Fuji Silysia FL-60D 1600 g, IPA:hexane=3:40). Fractions containing substantially no impurities were collected and evaporated to give benzyl 7-[(2R,4aR,5R,7aR)-2-(1,1-difluoropentyl)-2-hydroxy-6-oxooctahydrocyclopenta[b]pyran-5-yl]heptanate (2) (25.68 g, 53.44 mmol, yield: 75.8%).

EXAMPLE 2

To a solution of benzyl 7-{(1R,2R,3R)-2-[(6s)-4,4-difluoro-6-methyl-3-oxooctyl]-5-oxo-3-(2-tetrahydropyranyloxy)cyclopentyl}heptanoate(3) (62.76 g, 108.4 mmol) in acetonitrile (628 ml), water (62.8 ml) and 85% aqueous phosphoric acid (62.8 ml) were added and the mixture was stirred for about two hours at about 22° C. 10% aqueous sodium chloride (628 ml) was added to the mixture and the mixture was extracted with ethyl acetate (250 ml) for 3 times. The organic layers were combineded and washed with 10% aqueous sodium chloride (300 ml), saturated aqueous sodium bicarbonate (300 ml) and saturated aqueous sodium chloride (300 ml) successively, and dried with anhydrous magnesium sulfate(50 g). The reaction mixture was concentrated under reduced pressure and the residue was purified by silica gel column chromatography (Fuji Silysia BW-300 1800 g, ethyl acetate:hexane=1:4). Obtained fractions were purified again by silica gel column chromatography (Merck Art. 9385 2000 g, 2-propanol:hexane=1:20) to give benzyl 7-{(4aR,5R,7aR)-2-[(3S)-1,1-difluoro-3-methylpentyl]-2-hydroxy-6-oxooctahydrocyclopenta[b]pyran-5-yl}heptanate(4) (49.44 g, 99.96 mmol, yield: 92.2%).

COMPARATIVE EXAMPLE 2

Conventional Method Using Acetic Acid.

To benzyl 7-{(1R,2R,3R)-2-[(6S)-4,4-difluoro-6-methyl-3-oxyoctyl]]-5-oxo-3-(2-tetrahydropyranyloxy) cyclopentyl})heptanoate (3) (21.42 g, 37.01 mmol), tetrahydrofuran (50 ml), acetic acid (150 ml) and water (50 ml) were added and dissolved. The mixed solution was stirred at about 50° C. for 2.5 hours. The reaction mixture was concentrated under reduced. Water (200 ml) was added to the residue and the mixture was extracted with ether (150 ml+80 ml×2). The organic layer was washed twice with aqueous sodium bicarbonate (100 ml) and then with saturated aqueous sodium chlride (100 ml), and dried with anhydrous magnesium sulfate. The resulting mixture was concentrated under reduced pressure and purified by silica gel column chromatography (Merck Art.9385, 550 g, ethyl acetate:hexane=2:7). Fractions containing impurities were further purified by silica gel column chromatography (Merck Art. 9385, 210 g, ethyl acetate:hexane=1:4). Fractions still containing impurities were further purified by silica gel column chromatography(Merck Art. 9385, 100 g, ethyl acetate:hexane=1:4) to give benzyl 7-{(4aR,5R,7aR)-2-[(3S)-1,1-difluoro-3-methylpentyl]-2-hydroxy-6-oxooctahydrocyclopenta[b]pyran-5-yl}heptanate (4) (14.57 g, 29.46 mmol, yield: 79.6%).

Test Examples

Method

250mg of compound 1 was weighted and added to a 20 ml reaction container. Predetermined amounts of reaction solvent and water were added to the container and the mixture was stirred with magnetic stirrer. A predetermined amount of an acid catalyst was then added thereto and at the same time, sample of reaction mixture was obtained. (In test example 1 wherein phosphoric acid was used, the reaction proceeded very quickly and sample was obtained just before adding phosphoric acid catalyst.) The reaction was conducted in a temperature controlled bath with sampling at 30, 60, 90, 130, 180, 240 and 300 minutes for all examples and further at 360, 420, 480 and 540 minutes for test example 4 after the reaction was started. Component analysis of the obtained sample by means of liquid chromatography was conducted immediately after the sampling.

Component Analysis

About 50 μl of the reaction was sampled and mixed with acetonitrile (HPLC grade) (0.4 ml) to give sample solution. The solution (40 μl) was injected into the column and analyzed according to the following condition:

Column: YMC-Pack ODS-A A-312 S-5 μm 120A 6×150 mm Column temperature: constant temperature around 35° C. mobile phase: acetonitrile:distilled water(HPLC grade)=75:25 (v/v)

Flow rate:1.0 mL/min

Detector: differential refractometer (RI detector)

The amount of each component was calculated based on the RI area.

Figure 1:
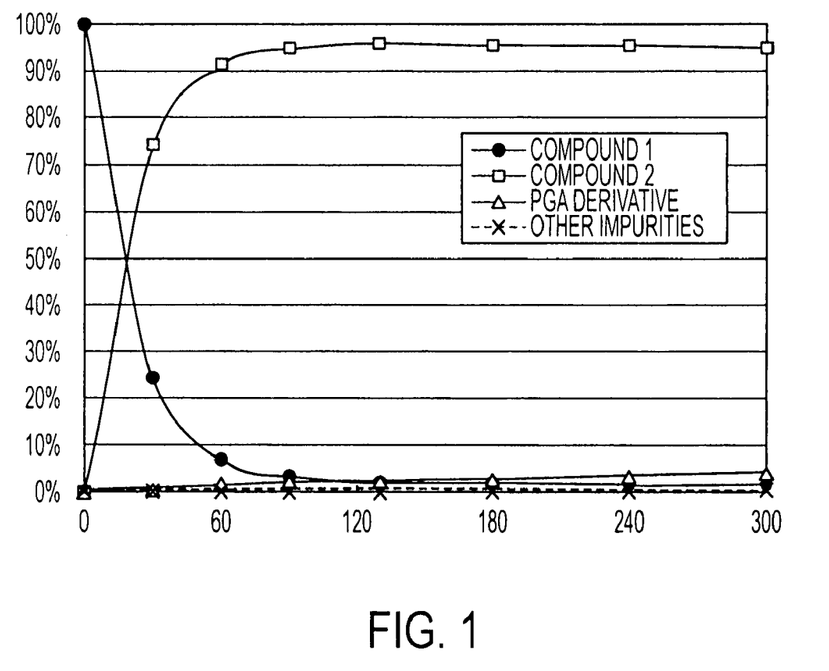
FIG. 1 shows result of test example 1, wherein the hydrolytic reaction was conducted using phosphoric acid at 20° C. The graph represents change of components in the reaction mixture with time.
Figure 2:
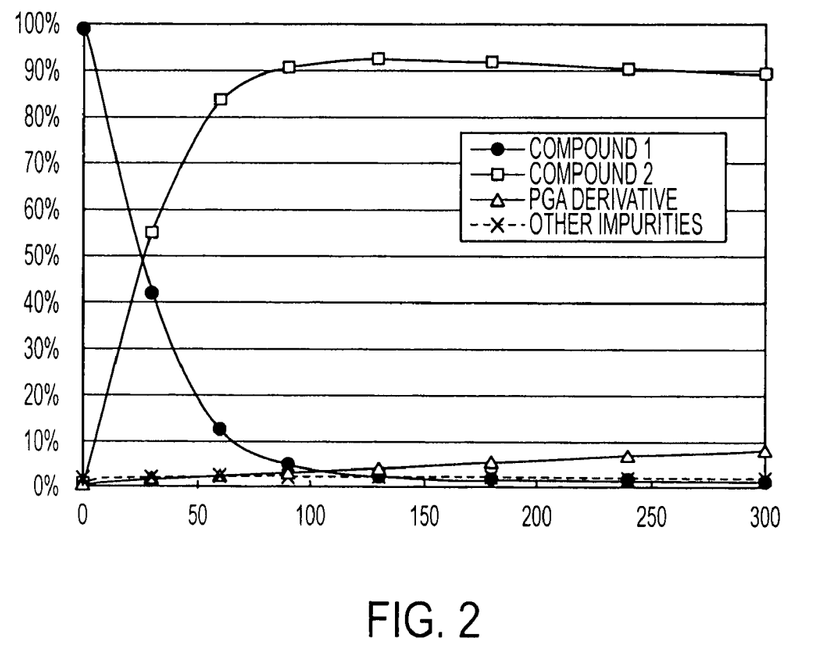
FIG. 2 shows result of test example 2, wherein the hydrolytic reaction was conducted using acetic acid at 50° C. The graph represents change of components in the reaction mixture with time.
Figure 3:
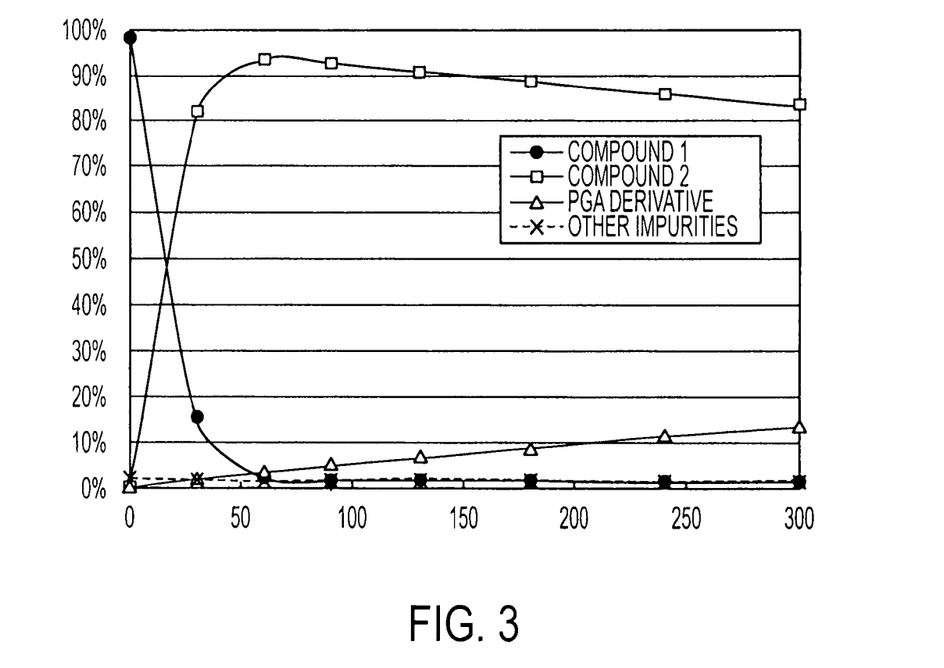
FIG. 3 shows result of test example 3, wherein the hydrolytic reaction was conducted using acetic acid at 55° C. The graph represents change of components in the reaction mixture with time.
Figure 4:
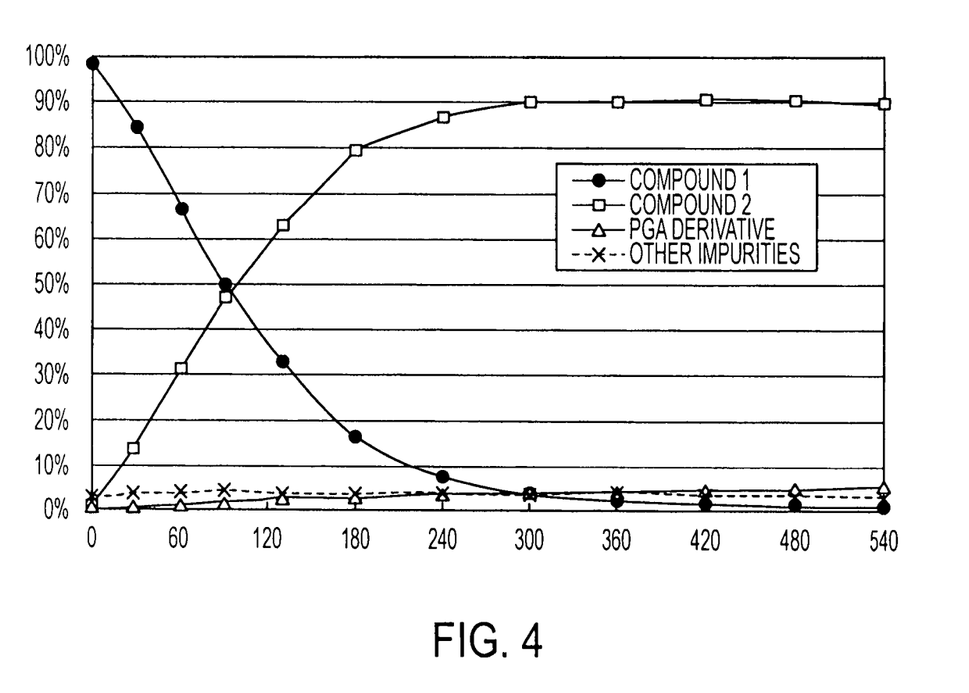
FIG. 4 shows result of test example 4, wherein the hydrolytic reaction was conducted using acetic acid at 40° C. The graph represents change of components in the reaction mixture with time.

Results of each example are shown in Tables 1-4 and FIGS. 1-4.

Test Example 1

This Invention

| Reaction condition | |
|---|---|
|  | amount per 1 g of compound 1 |
| acetonitrile | 10 |
| water | 1 |
| 85% aqueous phosphoric acid | 1 |
| Reaction temperature | 20° C. |

Test Example 2

Comparative

| Reaction condition | |
|---|---|
|  | amount per 1 g of compound 1 |
| tetrahydrofuran | 1 |
| water | 3.5 |
| acetic acid | 6.5 |
| Reaction temperature | 50° C. |

Test Example 3

Comparative

| Reaction condition | |
|---|---|
|  | amount per 1 g of compound 1 |
| tetrahydrofuran | 1 |
| water | 3.5 |
| acetic acid | 6.5 |
| Reaction temperature | 55° C. |

EXAMPLE 4

Comparative

| Reaction condition | |
|---|---|
|  | amount per 1 g of compound 1 |
| tetrahydrofuran | 1 |
| water | 3.5 |
| acetic acid | 6.5 |
| Reaction temperature | 40° C. |

Results

Example 1: Hydrolytic reaction was conducted using phosphoric acid catalyst at 20° C.

TABLE 1

Change of components in the reaction mixture with time:

| Reaction Time (min) | Components in the reaction mixture (%) (HPLC analysis, RI area percent) | | | |
|---|---|---|---|---|
|  | Compound 1 | Compound 2 | PGA derivative | Other impurities |
| 0 | 99.8 | 0.0 | 0.0 | 0.2 |
| 30 | 24.3 | 74.4 | 1.1 | 0.2 |
| 60 | 6.8 | 91.4 | 1.7 | 0.2 |
| 90 | 3.1 | 94.6 | 2.1 | 0.2 |
| 130 | 1.9 | 95.6 | 2.3 | 0.2 |
| 180 | 1.8 | 95.1 | 2.8 | 0.3 |
| 240 | 1.5 | 94.8 | 3.5 | 0.3 |
| 300 | 1.6 | 94.2 | 4.0 | 0.2 |

As is shown in Table 1, the hydrolytic reaction using phosphoric acid as acid catalyst proceeded very quickly and achieved to enough chemical conversion ratio within a short period of time even at an ambient temperature (20° C.). The amount of PGA derivative or other impurities were extremely small and the product was stable over time, even after the chemical conversion was completed. According to the method of the invention, the desired deprotected product can be manufactured in good and stable yield and quality, and therefore, the method is suitably applicable to a large scale production.

Test Example 2: Hydrolytic Reaction was Conducted using Acetic Acid Catalyst at 50° C.

TABLE 2

Change of components in the reaction mixture with time:

Components in the reaction mixture (%)
(HPLC analysis, RI area percent)

| Reaction Time (min) | Compound 1 | Compound 2 | PGA derivative | Other impurities |
|---|---|---|---|---|
| 0 | 98.6 | 0.0 | 0.0 | 1.4 |
| 30 | 41.9 | 55.2 | 1.2 | 1.6 |
| 60 | 12.3 | 83.9 | 2.1 | 1.8 |
| 90 | 4.4 | 90.8 | 2.9 | 1.8 |
| 130 | 1.8 | 92.4 | 3.9 | 2.0 |
| 180 | 1.0 | 91.9 | 5.2 | 1.9 |
| 240 | 1.0 | 90.5 | 6.7 | 1.8 |
| 300 | 0.8 | 89.1 | 8.3 | 1.8 |

Test Example 3 Hydrolytic Reaction was Conducted using Acetic Acid Catalyst at 55° C.

TABLE 3

Change of components in the reaction mixture with time:

Components in the reaction mixture (%)
(HPLC analysis, RI area percent)

| Reaction Time (min) | Compound 1 | Compound 2 | PGA derivative | Other impurities |
|---|---|---|---|---|
| 0 | 98.1 | 0.0 | 0.0 | 1.9 |
| 30 | 15.1 | 81.5 | 1.8 | 1.5 |
| 60 | 2.1 | 93.3 | 3.1 | 1.5 |
| 90 | 1.3 | 92.5 | 4.8 | 1.5 |
| 130 | 1.4 | 90.5 | 6.6 | 1.5 |
| 180 | 1.2 | 88.5 | 8.6 | 1.6 |
| 240 | 1.1 | 86.0 | 11.5 | 1.5 |
| 300 | 1.5 | 83.3 | 13.7 | 1.5 |

As is apparent from Tables 2 and 3, in order to proceed the hydrolytic reaction using acetic acid as a catalyst in a speed comparative to the reaction using phosphoric acid, the reaction temperature must be 50 to 55° C. However, under those conditions, the generation of the byproduct, PGA derivative proceeded quickly and the prolonged the reaction time caused a large amount of PGA derivative. The components in the reaction mixture were changed even during the analysis.

It can be said that those conditions are not suitable for the large scale production considering the difficulty in stopping the reaction at a right timing. That is, in case large scale production, cooling the reaction mixture takes quite a long time and therefore, yield and/or quality of the product will vary depending of the reaction time.

Example 4: Hydrolytic Reaction was Conducted using Acetic Acid Catalyst at 40° C.

TABLE 4

Change of components in the reaction mixture with time:

Components in the reaction mixture (%)
(HPLC analysis, RI area percent)

| Reaction Time (min) | Compound 1 | Compound 2 | PGA derivative | Other impurities |
|---|---|---|---|---|
| 0 | 97.7 | 0.0 | 0.0 | 2.3 |
| 30 | 83.8 | 13.1 | 0.3 | 2.8 |
| 60 | 65.7 | 30.6 | 0.7 | 3.0 |
| 90 | 49.1 | 46.1 | 1.3 | 3.5 |
| 130 | 32.3 | 62.5 | 1.9 | 3.4 |
| 180 | 15.7 | 78.8 | 2.3 | 3.3 |
| 240 | 7.2 | 86.3 | 3.1 | 3.4 |
| 300 | 3.4 | 89.6 | 3.7 | 3.3 |
| 360 | 2.1 | 89.6 | 4.1 | 4.1 |
| 420 | 1.4 | 90.4 | 4.7 | 3.5 |
| 480 | 1.1 | 90.4 | 5.1 | 3.5 |
| 540 | 1.0 | 89.6 | 5.9 | 3.6 |

In order to suppress the speed of generating PGA derivative in the conventional hydrolytic reaction using actic acid as a catalyst, the reaction temperature must be around 40° C. However, as shown in table 4, extremely long time period is required for achieving enough chemical conversion.

What is claimed is:

1. A method for preparing a 15-keto-prostaglandin E derivative represented by formula (I):

wherein, $R_1$ is a saturated or unsaturated bivalent lower or medium aliphatic hydrocarbon residue, which unsubstituted or substituted with halogen, lower alkyl, hydroxy, oxo, aryl or heterocyclic, and at least one of carbon atom in the aliphatic hydrocarbon is optionally substituted by oxygen, nitrogen or sulfur;

$R_2$ is a saturated or unsaturated lower or medium aliphatic hydrocarbon, which is unsubstituted or substituted with lower alkyl, lower alkoxy, lower alkanoyloxy, cyclo(lower)alkyl, cyclo(lower)alkyloxy, aryl, aryloxy, heterocyclic or heterocyclicoxy group; cyclo(lower)alkyl; cyclo(lower)alkyloxy; aryl; aryloxy; heterocyclic; or heterocyclicoxy group;

B is —$CH_2$—$CH_2$—, —CH=CH— or —C≡C—;

Q is —$CH_3$, —$COCH_3$, —OH, —COOH or a salt, ether, ester or amide thereof;

$X_1$ and $X_2$ are hydrogen, lower alkyl, or halogen;

which comprises the step of hydrolyzing the compound represented by formula (II):

(II)

wherein,
A₁ is a protecting group for hydroxy group, $R_1$, $R_2$, B, Q, $X_1$ and $X_2$ are the same as above in the presence of phosphoric acid compound.

2. The method of claim 1, wherein at least one of $X_1$ and $X_2$ is halogen.

3. The method of claim 1, wherein both of $X_1$ and $X_2$ are halogen.

4. The method of claim 1, wherein $X_1$ and $X_2$ are fluorine.

5. The method of claim 1, wherein the phosphoric acid compound is phosphoric acid.

6. The method of claim 1, wherein said step is conducted at a temperature from about 0° C. to 35° C.

7. The method of claim 1, wherein the reaction time of said step is about 1 to 6 hours.

* * * * *